(12) United States Patent
Kim et al.

(10) Patent No.: US 12,431,116 B2
(45) Date of Patent: Sep. 30, 2025

(54) APPARATUS FOR GENERATING DRIVING SOUND IN VEHICLE AND METHOD THEREOF

(71) Applicants: Hyundai Motor Company, Seoul (KR); Kia Corporation, Seoul (KR)

(72) Inventors: Ki Chang Kim, Gyeonggi-do (KR); Jin Sung Lee, Gyeonggi-do (KR); Dong Chul Park, Gyeonggi-do (KR); Eun Soo Jo, Gyeonggi-do (KR); Sang Jin Hong, Gyeonggi-do (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 159 days.

(21) Appl. No.: 17/745,646

(22) Filed: May 16, 2022

(65) Prior Publication Data

US 2023/0064483 A1 Mar. 2, 2023

(30) Foreign Application Priority Data

Sep. 1, 2021 (KR) .................. 10-2021-0116582

(51) Int. Cl.
| | | |
|---|---|---|
| G10K 15/04 | (2006.01) | |
| A61B 5/0205 | (2006.01) | |
| A61B 5/024 | (2006.01) | |
| A61B 5/026 | (2006.01) | |
| A61B 5/369 | (2021.01) | |
| G06F 3/16 | (2006.01) | |

(52) U.S. Cl.
CPC .......... G10K 15/04 (2013.01); A61B 5/02055 (2013.01); A61B 5/024 (2013.01); A61B 5/026 (2013.01); A61B 5/369 (2021.01); G06F 3/165 (2013.01)

(58) Field of Classification Search
CPC .... G10K 15/04; A61B 5/369; A61B 5/02055; A61B 5/024; A61B 5/026; G06F 3/165
See application file for complete search history.

(56) References Cited

U.S. PATENT DOCUMENTS

| | | |
|---|---|---|
| 8,155,343 B2 | 4/2012 | Honji et al. |
| 8,416,963 B2 | 4/2013 | Park et al. |
| 9,694,746 B2 | 7/2017 | Jo et al. |
| 10,960,816 B2 | 3/2021 | Lee et al. |
| 11,260,879 B2 | 3/2022 | Lee et al. |

(Continued)

FOREIGN PATENT DOCUMENTS

| | | |
|---|---|---|
| KR | 10-1081159 B1 | 11/2011 |
| KR | 10-2016-0060985 A | 5/2016 |

(Continued)

*Primary Examiner* — Daniel R Sellers
(74) *Attorney, Agent, or Firm* — Fox Rothschild LLP (57) ABSTRACT

An apparatus for generating a driving sound in a vehicle includes a first conversion device that receives first sound information and converts the received first sound information into second sound information, a second conversion device that converts the second sound information into third sound information based on a conversion parameter, a storage that receives feedback information of a user about the third sound information and corrects and stores the third sound information, and a playback device that plays the stored third sound information.

20 Claims, 5 Drawing Sheets

(56) References Cited

U.S. PATENT DOCUMENTS

| | | | |
|---|---|---|---|
| 2004/0044291 A1* | 3/2004 | Yasushi | A61B 5/18 600/509 |
| 2009/0049979 A1* | 2/2009 | Naik | G10H 1/40 84/636 |
| 2010/0329477 A1 | 12/2010 | Park et al. | |
| 2014/0069262 A1* | 3/2014 | Cheever | G10H 1/38 84/613 |
| 2016/0144782 A1 | 5/2016 | Jo et al. | |
| 2019/0362696 A1* | 11/2019 | Balassanian | G06F 16/68 |
| 2020/0215294 A1* | 7/2020 | Lee | B60Q 3/745 |
| 2020/0216093 A1 | 7/2020 | Lee et al. | |
| 2020/0324697 A1* | 10/2020 | Lee | B60W 40/08 |
| 2022/0108675 A1* | 4/2022 | Brockwell | G10H 1/46 |
| 2023/0394989 A1* | 12/2023 | Hill | G07C 5/02 |

FOREIGN PATENT DOCUMENTS

| | | |
|---|---|---|
| KR | 10-2020-0085969 A | 7/2020 |
| KR | 10-2020-0123503 A | 10/2020 |
| KR | 10-2232205 B1 | 3/2021 |

* cited by examiner

APPARATUS FOR GENERATING DRIVING SOUND IN VEHICLE AND METHOD THEREOF

CROSS-REFERENCE TO RELATED APPLICATION

This application claims under 35 U.S.C. § 119(a) the benefit of Korean Patent Application No. 10-2021-0116582, filed in the Korean Intellectual Property Office on Sep. 1, 2021, the entire contents of which are incorporated herein by reference.

BACKGROUND

(a) Technical Field

The present disclosure relates to an apparatus for generating a driving sound in a vehicle and a method thereof.

(b) Description of the Related Art

A driving sound of a vehicle may correspond to a sound generated according to driving of the vehicle. For example, the driving sound of the vehicle may indicate an engine sound of the vehicle, a music sound in the vehicle, an alarm sound of the vehicle, or the like, which may be generated during driving of the vehicle. The driving sound of the vehicle may be naturally generated or may be artificially generated. Because an existing vehicle driving sound typically is unchanged according to a model of the vehicle, it is unable to reflect personal preference of a user (or driver) of the vehicle.

Furthermore, although a driving sound according to personal preference of the user is artificially generated, when feedback of the user is not reflected in the generated driving sound and the generated driving sound is not corrected, the personal preference may not be suitably reflected in the driving sound.

SUMMARY

An aspect of the present disclosure provides an apparatus or a method for reflecting personal preference of a user of a vehicle in generating a driving sound of the vehicle.

Furthermore, another aspect of the present disclosure provides an apparatus or a method for reflecting feedback of a user of a vehicle in generating a driving sound of the vehicle.

The technical problems to be solved by the present disclosure are not limited to the aforementioned problems, and any other technical problems not mentioned herein will be clearly understood from the following description by those skilled in the art to which the present disclosure pertains.

According to an aspect of the present disclosure, an apparatus for generating a driving sound in a vehicle may include a first conversion device that receives first sound information and converts the received first sound information into second sound information, a second conversion device that converts the second sound information into third sound information based on a conversion parameter, a storage that receives feedback information of a user about the third sound information and correct and stores the third sound information, and a playback device that plays the stored third sound information.

Furthermore, according to embodiments, the first sound information may include one or more intervals. The second sound information may include at least one interval selected based on one of a first algorithm or a second algorithm among the one or more intervals included in the first sound information.

Furthermore, according to embodiments, the at least one interval selected based on the first algorithm may include an interval selected based on a convolutional neural network (CNN) algorithm among the one or more intervals. The at least one interval selected based on the second algorithm may include an interval selected based on request information of the user among the one or more intervals.

Furthermore, according to embodiments, the conversion parameter may include a first parameter used to convert the second sound information into the third sound information and a second parameter about information used to play the third sound information.

Furthermore, according to embodiments, the first parameter may include at least one of a pitch conversion parameter or a gain conversion parameter. The second parameter may include at least one of a power train (PT) rotation number parameter, a speed parameter, an acceleration parameter, or a torque parameter.

Furthermore, according to embodiments, the storage may include a classification device that classifies the third sound information, a feedback processing device that receives feedback information of the user about the classified third sound information and corrects the classified third sound information based on the received feedback information of the user, and a database that stores the corrected third sound information.

Furthermore, according to embodiments, the classified third sound information may indicate one of vehicle engine sound information, music sound information, alarm sound information, or voice information. The database may indicate one of a vehicle engine sound database, a music sound database, an alarm sound database, or a voice database.

Furthermore, according to embodiments, the classified third sound information may be classified based on a CNN algorithm.

Furthermore, according to embodiments, the feedback information of the user may indicate one of first feedback information indicative of correcting the classified third sound information or second feedback information indicative of not correcting the classified third sound information.

Furthermore, according to embodiments, the feedback information of the user may be determined as the first feedback information or the second feedback information, based on at least one of heart rate information, blood flow information, body temperature information, pulse information, or brainwave information of the user.

According to another aspect of the present disclosure, a method for generating a driving sound in a vehicle may include: receiving, by a first conversion device, first sound information and converting the received first sound information into second sound information; converting, by a second conversion device, the second sound information into third sound information based on a conversion parameter; receiving, by a storage, feedback information of a user about the third sound information and correcting and storing the third sound information; and playing, by a playback device, the stored third sound information.

Furthermore, according to embodiments, the first sound information may include one or more intervals. The second sound information may include at least one interval selected based on one of a first algorithm or a second algorithm among the one or more intervals included in the first sound information.

Furthermore, according to embodiments, the at least one interval selected based on the first algorithm may include an interval selected based on a CNN algorithm among the one or more intervals. The at least one interval selected based on the second algorithm may include an interval selected based on request information of the user among the one or more intervals. Furthermore, according to embodiments, the interval selected based on the request information of the user may indicate an interval randomly selected by the user among the intervals.

Furthermore, according to embodiments, the conversion parameter may include a first parameter used to convert the second sound information into the third sound information and a second parameter about information used to play the third sound information.

Furthermore, according to embodiments, the first parameter may include at least one of a pitch conversion parameter or a gain conversion parameter. The second parameter may include at least one of a power train (PT) rotation number parameter, a speed parameter, an acceleration parameter, or a torque parameter.

Furthermore, according to embodiments, the correcting and storing of the third sound information may include classifying the third sound information, receiving feedback information of the user about the classified third sound information and correcting the classified third sound information based on the received feedback information of the user, and storing the corrected third sound information in a database.

Furthermore, according to embodiments, the classified third sound information may indicate one of vehicle engine sound information, music sound information, alarm sound information, or voice information. The database may indicate one of a vehicle engine sound database, a music sound database, an alarm sound database, or a voice database.

Furthermore, according to embodiments, the classified third sound information may be classified based on a CNN algorithm.

Furthermore, according to embodiments, the feedback information of the user may be one of first feedback information indicative of correcting the classified third sound information or second feedback information indicative of not correcting the classified third sound information.

Furthermore, according to embodiments, the feedback information of the user may be determined as the first feedback information or the second feedback information, based on at least one of heart rate information, blood flow information, body temperature information, pulse information, or brainwave information of the user.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Hereinafter, some embodiments of the present disclosure will be described in detail with reference to the accompanying drawings. In adding the reference numerals to the components of each drawing, it should be noted that the identical component is designated by the identical numerals even when they are displayed on other drawings. Further, in describing the embodiment of the present disclosure, a detailed description of well-known features or functions will be ruled out in order not to unnecessarily obscure the gist of the present disclosure.

In describing the components of the embodiment according to the present disclosure, terms such as first, second, "A", "B", (a), (b), and the like may be used. These terms are merely intended to distinguish one component from another component, and the terms do not limit the nature, sequence or order of the constituent components. Furthermore, unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

Hereinafter, embodiments of the present disclosure will be described in detail with reference to FIGS. 1 to 5.

Figure 1:
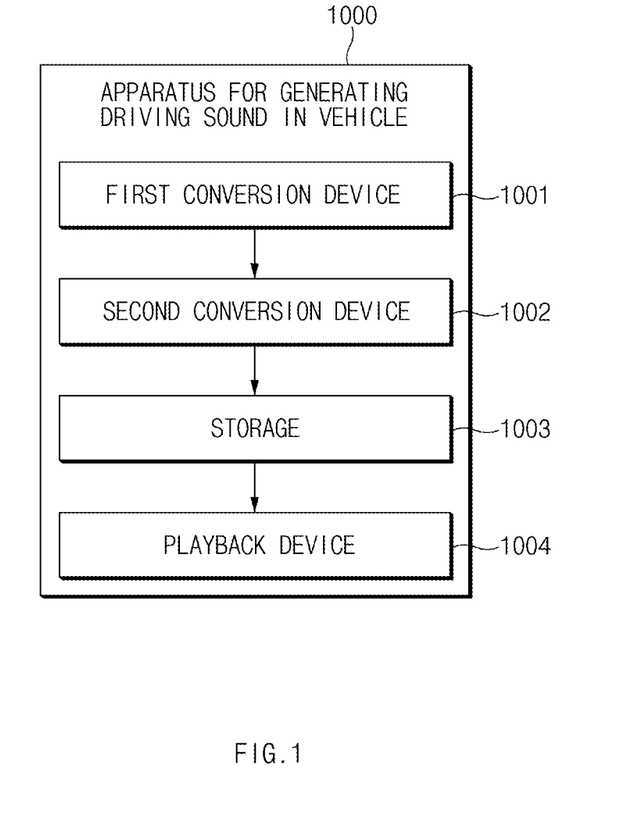
FIG. 1 illustrates an example of an apparatus for generating a driving sound in a vehicle according to embodiments.

FIG. 1 illustrates an example of an apparatus for generating a driving sound in a vehicle according to embodiments.

In particular, FIG. 1 is a block diagram illustrating an example of an apparatus 1000 for generating a driving sound in a vehicle according to embodiments.

The driving sound of the vehicle may indicate a sound generated according to the driving of the vehicle. For example, the driving sound of the vehicle may indicate an engine sound of the vehicle, a music sound in the vehicle, an alarm sound of the vehicle, or the like, which is generated according to the driving of the vehicle. The driving sound of the vehicle may be naturally generated or may be artificially generated. Because an existing vehicle driving sound is constant according to a model of the vehicle, it is unable to reflect personal preference of a user (or driver) of the vehicle in the existing vehicle driving sound.

Furthermore, although the driving sound according to personal preference is artificially generated, when feedback of the user is not reflected in the generated driving sound and the generated driving sound is not corrected, the personal preference is not suitably reflected in the driving sound.

The apparatus 1000 according to embodiments may reflect personal preference of the user of the vehicle in generating a driving sound of the vehicle. Furthermore, the apparatus 1000 according to embodiments may reflect feedback of the user of the vehicle in generating a driving sound of the vehicle.

The apparatus 1000 for generating the driving sound in the vehicle according to embodiments may include a first conversion device 1001, a second conversion device 1002, a storage 1003, and/or a playback device 1004. The apparatus 1000 according to embodiments may further include one or more elements which are not shown in the drawing.

The apparatus 1000 according to embodiments may convert a sound selected by the user of the vehicle into a driving sound and may play the converted driving sound. In other words, the apparatus 1000 according to embodiments may select an interval suitable for being converted into a driving sound in a sound input by the user and may convert the selected interval into a driving sound of the vehicle.

The first conversion device 1001 may receive first sound information and may convert the received first sound information into second sound information.

The first sound information according to embodiments may be the sound selected by the user, which is described above. For example, the first sound information may indicate at least one of music, a sound, or a machine sound selected by the driver. The first sound information according to embodiments may include one or more intervals. In other words, the sound information input by the user may be composed of one or more intervals.

The second sound information according to embodiments may indicate an interval (or a portion) to be converted into a driving sound of the vehicle, in the first sound information input by the user, which is described above. The sound information according to embodiments may include at least one interval selected based on one of a first algorithm or a second algorithm among the one or more intervals included in the first sound information. A detailed description of the first algorithm or the second algorithm according to embodiments will be given below with reference to FIG. 2.

The second conversion device 1002 may convert the second sound information into third sound information, based on a conversion parameter. The third sound information according to embodiments may indicate the driving sound of the vehicle, which is described above. The conversion parameter according to embodiments may include a parameter considered to generate a driving sound of the vehicle based on the above-mentioned second sound information.

The storage 1003 according to embodiments may receive feedback information of the user about the third sound information and may correct and store the third sound information. The feedback information of the user according to embodiments may be information indicating feedback of the user (or the driver) on the above-mentioned driving sound. In other words, the apparatus 1000 may receive feedback information of the user about the generated driving sound and may correct and store the generated driving sound based on the received feedback information.

The playback device 1004 according to embodiments may play the stored third sound information which is described above. For example, the playback device 1004 may include a device including an amp speaker.

The apparatus 1000 according to embodiments may generate and play a vehicle driving sound in which personal preference of the user (or the driver) of the vehicle is reflected, by means of the method described in the drawing. In other words, the apparatus 1000 may generate and play a driving sound of the vehicle based on personal preference sound information input by the user of the vehicle. Furthermore, the apparatus 1000 may receive feedback information of the user about the generated (or played) driving sound and may correct the driving sound based on the received feedback information, thus better reflecting personal preference of the user.

Figure 2:
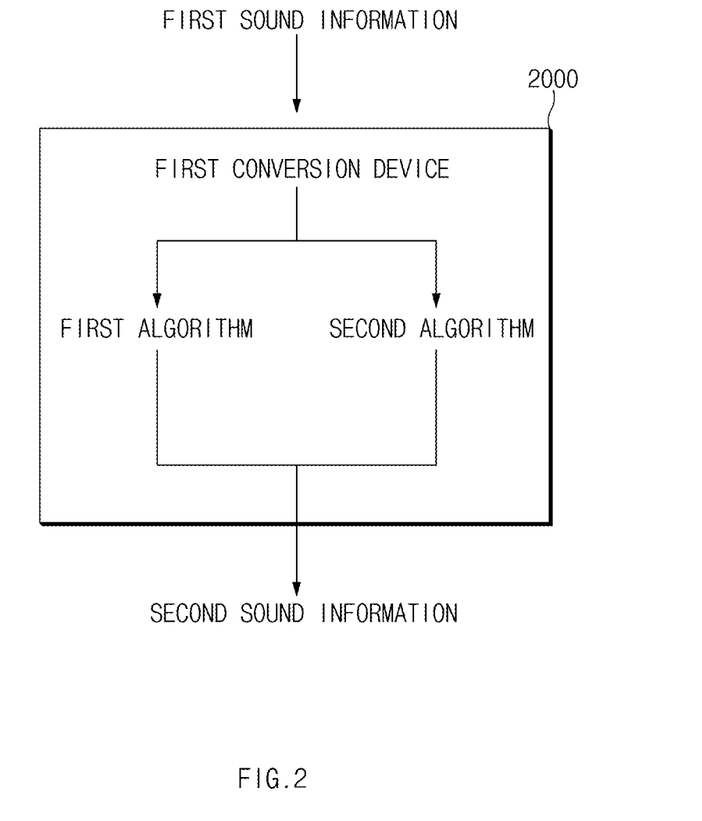
FIG. 2 illustrates an example of a first conversion device according to embodiments.

FIG. 2 illustrates an example of a first conversion device according to embodiments.

In particular, FIG. 2 is a block diagram illustrating an example of a first conversion device 2000 (e.g., a first conversion device 1001 described above with reference to FIG. 1).

As described above with reference to FIG. 1, the first conversion device 2000 may receive first sound information and may convert the received first sound information into second sound information. Furthermore, as described above with reference to FIG. 1, the sound information may include one or more intervals, and the second sound information may include at least one interval selected based on one of a first algorithm or a second algorithm among the one or more intervals included in the first sound information.

The first conversion device 2000 according to embodiments may receive the first sound information and may select an interval to be converted into a driving sound of a vehicle based on a selection of a user (a driver) or an artificial intelligence (AI) algorithm.

The at least one interval selected based on the first algorithm according to embodiments may include an interval selected based on a convolutional neural network (CNN) algorithm among the one or more intervals. Furthermore, the at least one interval selected based on the second algorithm according to embodiments may include an interval selected based on request information of the user among the one or more intervals.

For example, the first conversion device 2000 may identify, select, and convert an interval having the highest sound among the one or more intervals included in the first sound information by means of the CNN algorithm. Furthermore, for example, the first conversion device 2000 may select an interval selected by the user among the one or more intervals included in the first sound information and may convert the selected interval into second sound information.

For example, the first conversion device 2000 may calculate sound pressure (power) for each frequency, based on short-time Fourier transform with respect to the one or more intervals included in the first sound information. Thereafter, the first conversion device 2000 may select an interval having maximum sound pressure among the one or more intervals, using mean-pooling. Thereafter, the first conversion device 2000 may select interval(s) having the maximum sound pressure and may convert the selected interval(s) into second sound information.

The apparatus 1000 according to embodiments may generate and play a vehicle driving sound in which personal preference of the user (or the driver) of the vehicle is reflected, by means of the method described in the drawing. In other words, the apparatus 1000 may generate and play a driving sound of the vehicle based on personal preference sound information input by the user of the vehicle. Furthermore, the apparatus 1000 may receive feedback information of the user about the generated (or played) driving sound and may correct the driving sound based on the received feedback information, thus better reflecting personal preference of the user.

Figure 3:
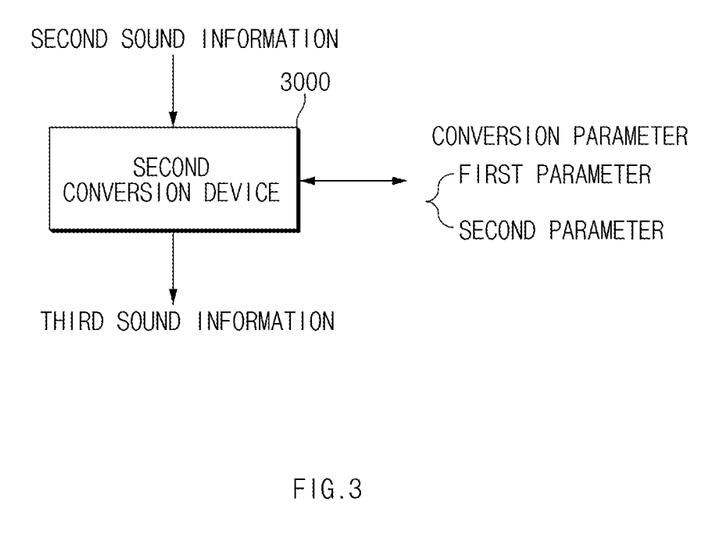
FIG. 3 illustrates an example of a second conversion device according to embodiments.

FIG. 3 illustrates an example of a second conversion device according to embodiments.

In particular, FIG. 3 is a block diagram illustrating an example of a second conversion device 3000 (e.g., a second conversion device 1002 described above with reference to FIG. 2).

As described above with reference to FIG. 1, the second conversion device 3000 according to embodiments may convert second sound information into third sound information (e.g., the above-mentioned driving sound of the vehicle) based on a conversion parameter.

As described above with reference to FIGS. 1 and 2, the second sound information may indicate at least one of intervals included in the first sound information, which is selected to be converted into a driving sound of the vehicle. The second conversion device 3000 may convert the sound information converted by the first conversion device 2000 into a driving sound of the vehicle.

As described above with reference to FIG. 1, the conversion parameter according to embodiments may include a parameter considered to generate a driving sound of the vehicle based on the above-mentioned second sound information. The conversion parameter according to embodiments may include one or more parameters.

The conversion parameter according to embodiments may include a first parameter used to convert the second sound information into third sound information and a second parameter about information used to play the third sound information.

The first parameter according to embodiments may include a parameter about conversion applied to the second sound information to convert the second sound information into the third sound information. For example, the first parameter may include at least one of a pitch conversion parameter or a gain conversion parameter. An apparatus 1000 may adjust pitch of the second sound information based on the pitch conversion parameter. The apparatus 1000 may adjust a tone color of the second sound information based on the gain conversion parameter.

The second parameter according to embodiments may include a parameter about information considered to change a method for playing the generated driving sound (or the third sound information). For example, the second parameter may include at least one of a power train (PT) rotation number parameter, a speed parameter, an acceleration parameter, or a torque parameter. The apparatus 1000 may adjust playback of the third sound information depending on the number of PT rotations of the vehicle based on the PT rotation number parameter. The apparatus 1000 may adjust playback of the third sound information depending on a speed of the vehicle based on the speed parameter. The apparatus 1000 may adjust playback of the third sound information depending on acceleration of the vehicle based on the acceleration parameter. The apparatus 1000 may adjust playback of the third sound information depending to a torque value of the vehicle based on the torque parameter.

The apparatus 1000 according to embodiments may generate and play a vehicle driving sound in which personal preference of the user (or the driver) of the vehicle is reflected, by means of the method described in the drawing. In other words, the apparatus 1000 may generate and play a driving sound of the vehicle based on personal preference sound information input by the user of the vehicle. Furthermore, the apparatus 1000 may receive feedback information of the user about the generated (or played) driving sound and may correct the driving sound based on the received feedback information, thus better reflecting personal preference of the user.

Figure 4:
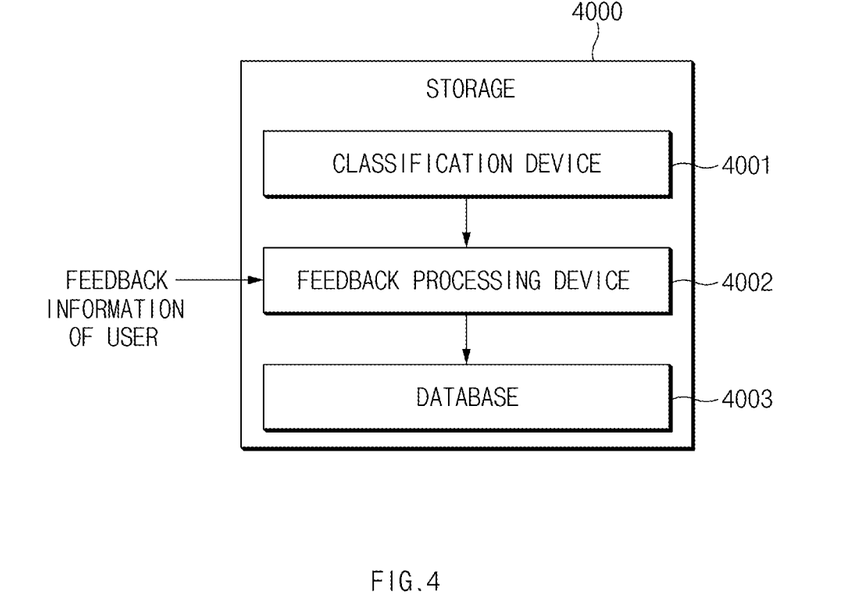
FIG. 4 illustrates an example of a storage according to various embodiments.

FIG. 4 illustrates an example of a storage according to various embodiments.

In particular, FIG. 4 is a block diagram illustrating an example of a storage 4000 (e.g., a storage 1003 described above with reference to FIG. 1).

As described above with reference to FIG. 1, the storage 4000 according to embodiments may receive feedback information about third sound information and may correct and store the third sound information.

The storage 4000 according to embodiments may include a classification device 4001, a feedback processing device 4002, and/or a database 4003. The storage 4000 according to embodiments may further include one or more elements which are not shown in the drawing.

The classification device 4001 according to embodiments may classify the third sound information.

As described above with reference to FIG. 1, a driving sound according to embodiments may indicate one of a vehicle engine sound, an alarm sound, or a voice. The third sound information may be classified according to input first sound information. In other words, based on a sound indicated by the first sound information input by a user, the classification device 4001 may classify the third sound information as a driving sound of the most similar type to the sound. In other words, the classified third sound information may indicate one of vehicle engine sound information, music sound information, alarm sound information, or voice information.

Thus, the database 4003 according to embodiments may indicate one of a vehicle engine sound database, a music sound database, an alarm sound database, or a voice database.

The third sound information according to embodiments may be classified based on an artificial intelligence algorithm. For example, the third sound information may be classified based on a CNN algorithm.

The feedback processing device 4002 according to embodiments may receive feedback information of the user about the classified third sound information and may correct the classified third sound information based on the received feedback information of the user. The feedback information of the user according to embodiments may be information indicating whether there is a correction request of the user for the played driving sound. For example, the feedback information of the user may indicate one of first feedback information indicative of correcting the classified third sound information or second feedback information indicative of not correcting the classified third sound information. In other words, the feedback processing device 4002 may feed back a driving sound generated based on the feedback information.

The feedback information according to embodiments may be received by one or more buttons included in the vehicle. The user may select buttons included in the vehicle and may input the above-mentioned feedback information. For example, the feedback processing device 4002 may receive the first feedback information in response to that the user selects a first button. Furthermore, the feedback processing device 4002 may receive the second feedback information in response to that the user selects a second button. The above-mentioned first button and/or second button may be a button included in the buttons included in the vehicle.

The feedback information according to embodiments may be determined as the first feedback information or the second feedback information, based on at least one of heart rate information, blood flow information, body temperature information, pulse information, or brainwave information of the user.

For example, the feedback processing device 4002 may store heart rate information, blood flow information, body temperature information, pulse information, and/or brainwave information of the user when the generated feedback information is the first feedback information. Furthermore, the feedback processing device 4002 may store heart rate information, blood flow information, body temperature information, pulse information, and/or brainwave information of the user when the generated feedback information is the second feedback information. Thereafter, the feedback processing device 4002 may measure heart rate information, blood flow information, body temperature information, pulse information, and/or brainwave information of the user and may determine whether the generated feedback information is the first feedback information or the second feedback information, using the measured heart rate information, blood flow information, body temperature information, pulse information, and/or brainwave information of the user.

The above-mentioned heart rate information, blood flow information, body temperature information, pulse information, and/or brainwave information of the user may be measured by one or more devices (e.g., a steering wheel) included in the vehicle.

The database 4003 according to embodiments may store the corrected third sound information.

Thus, the apparatus 1000 may play the third sound information stored in the database 4003 and may play a driving sound in which preference (e.g., feedback) of the user is reflected.

The apparatus 1000 according to embodiments may generate and play a vehicle driving sound in which personal preference of the user (or the driver) of the vehicle is reflected, by means of the method described in the drawing. In other words, the apparatus 1000 may generate and play a driving sound of the vehicle based on personal preference sound information input by the user of the vehicle. Furthermore, the apparatus 1000 may receive feedback information of the user about the generated (or played) driving sound and may correct the driving sound based on the received feedback information, thus better reflecting personal preference of the user.

Figure 5:
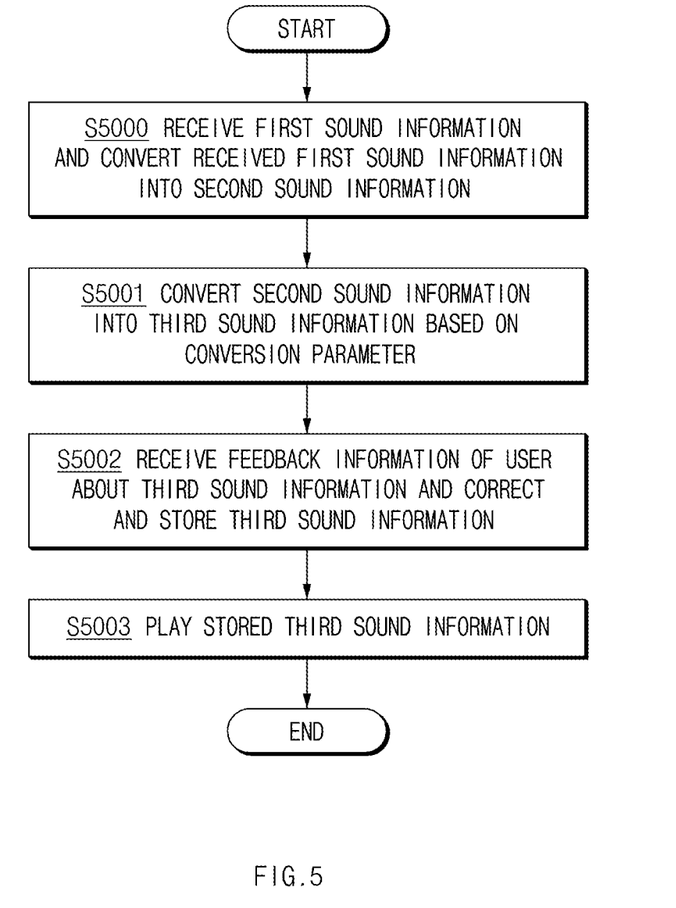
FIG. 5 is a flowchart illustrating an example of a method for generating a driving sound in a vehicle according to embodiments.

FIG. 5 is a flowchart illustrating an example of a method for generating a driving sound in a vehicle according to embodiments.

In particular, FIG. 5 is a flowchart illustrating an example of the method for generating the driving sound in the vehicle (or the method) according to embodiments. An apparatus 1000 described above with reference to FIGS. 1 to 4 may perform the method described in FIG. 5.

The method according to embodiments may include receiving (S5000) first sound information and converting the received first sound information into second sound information, converting (S5001) the second sound information into third sound information based on a conversion parameter, receiving (S5002) feedback information of a user about the third sound information and correcting and storing the third sound information, and/or playing (S5003) the stored third sound information. The method according to embodiments may further include one or more steps which are not described in the drawing.

The first sound information according to embodiments may include one or more intervals.

The second sound information according to embodiments may include at least one interval selected based on one of a first algorithm or a second algorithm among the one or more intervals included in the first sound information.

A description of the first sound information and the second sound information according to embodiments may be the same or similar to that described above with reference to FIGS. 1 to 3. A description of the first algorithm and the second algorithm according to embodiments may be the same or similar to that described above with reference to FIGS. 1 and 2.

The at least one interval selected based on the first algorithm according to embodiments may include an interval selected based on a CNN algorithm among the one or more intervals. The at least one interval selected based on the second algorithm according to embodiments may include an interval selected based on request information of the user among the one or more intervals.

The conversion parameter according to embodiments may include a first parameter used to convert the second sound information into the third sound information and a second parameter about information used to play the third sound information.

The first parameter according to embodiments may include at least one of a pitch conversion parameter or a gain conversion parameter. The second parameter according to embodiments may include at least one of a PT rotation number parameter, a speed parameter, an acceleration parameter, or a torque parameter. A description of the first parameter and the second parameter according to embodiments may be the same or similar to that described above with reference to FIGS. 1 to 3.

The correcting and storing of the third sound information may include classifying the third sound information, receiving feedback information of the user about the classified third sound information and correcting the classified third sound information based on the received feedback information of the user, and storing the corrected third sound information in a database 4003. A description of the above-mentioned steps may be the same or similar to that described above with reference to FIG. 4.

The classified third sound information according to embodiments may indicate one of vehicle engine sound information, music sound information, alarm sound information, or voice information.

The database 4003 according to embodiments may indicate one of a vehicle engine sound database, a music sound database, an alarm sound database, or a voice database.

The third sound information according to embodiments may be classified based on a CNN algorithm. A description of the third sound information and the CNN algorithm according to embodiments may be the same or similar to that described above with reference to FIGS. 1 to 3.

The feedback information of the user according to embodiments may indicate one of first feedback information indicative of correcting the classified third sound information or second feedback information indicative of not correcting the classified third sound information. A description of the feedback information of the user according to embodiments may be the same or similar to that described above with reference to FIG. 4.

The feedback information of the user according to embodiments may be determined as the first feedback information or the second feedback information, based on at least one of heart rate information, blood flow information, body temperature information, pulse information, or brainwave information of the user.

The apparatus 1000 according to embodiments may generate and play a vehicle driving sound in which personal preference of the user (or the driver) of the vehicle is reflected, by means of the method described in the drawing. In other words, the apparatus 1000 may generate and play a driving sound of the vehicle based on personal preference sound information input by the user of the vehicle. Furthermore, the apparatus 1000 may receive feedback information of the user about the generated (or played) driving sound and may correct the driving sound based on the received feedback information, thus better reflecting personal preference of the user.

Embodiments may reflect personal preference of the user of the vehicle in generating a driving sound of the vehicle.

Furthermore, embodiments may reflect feedback of the user of the vehicle in generating a driving sound of the vehicle.

In addition, various effects ascertained directly or indirectly through the present disclosure may be provided.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, the exemplary embodiments of the present disclosure are provided to explain the spirit and scope of the present disclosure, but not to limit them, so that the spirit and scope of the present disclosure is not limited by the embodiments. The scope of the present disclosure should be construed on the basis of the accompanying claims, and all the technical ideas within the scope equivalent to the claims should be included in the scope of the present disclosure.

What is claimed is:

1. An apparatus for generating a driving sound in a vehicle, the apparatus comprising:
   a first conversion device configured to receive first sound information and convert the received first sound information into second sound information;
   a second conversion device configured to convert the second sound information into third sound information based on a conversion parameter;
   a storage configured to receive feedback information of a user about the third sound information and correct and store the third sound information; and
   a playback device configured to play the stored third sound information according to driving of the vehicle,
   wherein the first conversion device is configured to:
      calculate sound pressure for each frequency, based on short-time Fourier transform with respect to one or more intervals included in the first sound information;
      select an interval having a maximum sound pressure among the one or more intervals; and
      convert the selected interval into the second sound information,
   wherein the first sound information includes a sound selected by a user,
   wherein the second sound information includes at least one interval to be converted into the driving sound of the vehicle, in the first sound information input by the user, and
   wherein the third sound information indicates the driving sound of the vehicle, and the third sound information is configured to be corrected based on the feedback information to reflect personal preference of the user.

2. The apparatus of claim 1,
   wherein the second sound information includes the at least one interval selected based on one of a first algorithm or a second algorithm among the one or more intervals included in the first sound information.

3. The apparatus of claim 2, wherein the at least one interval selected based on the first algorithm includes an interval selected based on a convolutional neural network (CNN) algorithm among the one or more intervals, and
   wherein the at least one interval selected based on the second algorithm includes an interval selected based on request information of the user among the one or more intervals.

4. The apparatus of claim 1, wherein the conversion parameter includes a first parameter used to convert the second sound information into the third sound information and a second parameter about information used to play the third sound information.

5. The apparatus of claim 4, wherein the first parameter includes at least one of a pitch conversion parameter or a gain conversion parameter, and
   wherein the second parameter includes at least one of a power train (PT) rotation number parameter, a speed parameter, an acceleration parameter, or a torque parameter.

6. The apparatus of claim 1, wherein the storage includes:
   a classification device configured to classify the third sound information;
   a feedback processing device configured to receive feedback information of the user about the classified third sound information and correct the classified third sound information based on the received feedback information of the user; and a database configured to store the corrected third sound information.

7. The apparatus of claim 6, wherein the classified third sound information indicates one of vehicle engine sound information, music sound information, alarm sound information, or voice information, and
wherein the database indicates one of a vehicle engine sound database, a music sound database, an alarm sound database, or a voice database.

8. The apparatus of claim 7, wherein the classified third sound information is classified based on a CNN algorithm.

9. The apparatus of claim 6, wherein the feedback information of the user indicates one of first feedback information indicative of correcting the classified third sound information or second feedback information indicative of not correcting the classified third sound information.

10. The apparatus of claim 9, wherein the feedback information of the user is determined as the first feedback information or the second feedback information, based on at least one of heart rate information, blood flow information, body temperature information, pulse information, or brainwave information of the user.

11. A method for generating a driving sound in a vehicle, the method comprising:
receiving, by a first conversion device, first sound information and converting the received first sound information into second sound information;
converting, by a second conversion device, the second sound information into third sound information based on a conversion parameter;
receiving, by a storage, feedback information of a user about the third sound information and correcting and storing the third sound information; and
playing, by a playback device, the stored third sound information according to driving of the vehicle,
wherein converting the received first sound information into the second sound information includes:
calculating, by the first conversion device, sound pressure for each frequency, based on short-time Fourier transform with respect to one or more intervals included in the first sound information;
selecting, by the first conversion device, an interval having a maximum sound pressure among the one or more intervals; and
converting, by the first conversion device, the selected interval into the second sound information,
wherein the first sound information includes a sound selected by a user,
wherein the second sound information includes at least one interval to be converted into the driving sound of the vehicle, in the first sound information input by the user, and
wherein the third sound information indicates the driving sound of the vehicle, and the third sound information is configured to be corrected based on the feedback information to reflect personal preference of the user.

12. The method of claim 11,
wherein the second sound information includes the at least one interval selected based on one of a first algorithm or a second algorithm among the one or more intervals included in the first sound information.

13. The method of claim 12, wherein the at least one interval selected based on the first algorithm includes an interval selected based on a CNN algorithm among the one or more intervals, and
wherein the at least one interval selected based on the second algorithm includes an interval selected based on request information of the user among the one or more intervals.

14. The method of claim 11, wherein the conversion parameter includes a first parameter used to convert the second sound information into the third sound information and a second parameter about information used to play the third sound information.

15. The method of claim 14, wherein the first parameter includes at least one of a pitch conversion parameter or a gain conversion parameter, and
wherein the second parameter includes at least one of a power train (PT) rotation number parameter, a speed parameter, an acceleration parameter, or a torque parameter.

16. The method of claim 11, wherein the correcting and storing of the third sound information includes:
classifying the third sound information;
receiving feedback information of the user about the classified third sound information and correcting the classified third sound information based on the received feedback information of the user; and
storing the corrected third sound information in a database.

17. The method of claim 16, wherein the classified third sound information indicates one of vehicle engine sound information, music sound information, alarm sound information, or voice information, and
wherein the database indicates one of a vehicle engine sound database, a music sound database, an alarm sound database, or a voice database.

18. The method of claim 17, wherein the classified third sound information is classified based on a CNN algorithm.

19. The method of claim 16, wherein the feedback information of the user is one of first feedback information indicative of correcting the classified third sound information or second feedback information indicative of not correcting the classified third sound information.

20. The method of claim 19, wherein the feedback information of the user is determined as the first feedback information or the second feedback information, based on at least one of heart rate information, blood flow information, body temperature information, pulse information, or brainwave information of the user.

* * * * *